United States Patent [19]

Chiusoli et al.

[11] 4,309,357
[45] Jan. 5, 1982

[54] PROCESS FOR PREPARING DIENOIC ACIDS

[75] Inventors: Gian P. Chiusoli, Parma; William Giroldini, Bibbiano; Giuseppe Salerno, Parma, all of Italy

[73] Assignee: Montedison S.p.A., Milan, Italy

[21] Appl. No.: 128,083

[22] Filed: Mar. 7, 1980

[30] Foreign Application Priority Data

Mar. 8, 1979 [IT] Italy ................................ 20824 A/79

[51] Int. Cl.$^3$ ............................................. C07C 51/00
[52] U.S. Cl. ..................................... 260/413; 562/495; 562/598; 562/599; 562/601
[58] Field of Search ........ 260/413 R, 413 K, 413 HC; 562/495, 598, 601, 599

[56] References Cited

U.S. PATENT DOCUMENTS

| | | | |
|---|---|---|---|
| 3,326,936 | 6/1967 | Allingham | 260/413 K |
| 3,493,590 | 2/1970 | Chahardes | 260/413 HC |
| 4,105,705 | 8/1978 | Larock | 562/598 |

FOREIGN PATENT DOCUMENTS 938963 10/1963 United Kingdom .

OTHER PUBLICATIONS

Wadsworth et al., J.A.C.S., vol. 83, pp. 1733–1738, (1960).

*Primary Examiner*—John F. Niebling

[57] ABSTRACT

Dienoic acids are prepared by reaction of salts of 3-butenoic acid and vinyl halides, in the presence of catalysts which are phosphinic complexes of rhodium or nickel.

12 Claims, No Drawings

PROCESS FOR PREPARING DIENOIC ACIDS

THE PRIOR ART

We are not aware of any prior description or suggestion of the reaction involved in the process for preparing dienoic acids described and claimed herein.

According to the prior art which is known, 2,6-dienoic acids can be obtained by alternative processes involving different reactions and based on the Witting synthesis starting with γ-δ-unsaturated aldehydes and reacting said aldehydes with carboalkoxy-triphenyl-phosphoranes.

However, techniques of that kind require the preliminary preparation of the γ-δ-unsaturated aldehydes which are difficult to prepare and not readily available, as well as the stoichiometric use of phosphorated intermediates which are objectionable from the viewpoint of compatibility of the effluents with present-day environmental protection requirements, etc., with the corresponding economical burdens that make such techniques substantially impractical from the industrial point of view.

Also known are catalytic processes for preparing dienoic acids by reacting unsaturated halides (vinyl-, allyl halides) with acetylene and carbon oxide in hydroxylated solvents, in the presence of nickel carbonyl or precursors thereof.

Those are all methods of low catalytic activity and, moreover, are of little industrial feasibility, due to the use of nickel carbonyl derivatives which are not suitable for industrial use because of their high toxicity.

Moreover, the unsaturated acids obtained according to that technique, since they have the double bonds in a prevailingly non-conjugated position, must subsequently be isomerized if dienoic acids with conjugated double bonds are desired.

THE PRESENT INVENTION

One object of this invention is to provide a simple and cheap process for the preparation of dienoic acids, having in particular the double bonds in a prevailingly conjugated position, and that are free of the drawbacks and disadvantages of the processes known in the prior art.

This and still other objects, which will appear even more clearly to the skilled in the art from the following description, are achieved, according to this invention, by a process for the preparation of dienoic acids, in particular of 3,5-dienoic acids, characterized in that a vinyl halide of the formula $$R-CH=CHX \quad (I),$$

wherein R represents either a hydrogen atom or a hydrocarbyl group having from 1 to 20 carbon atoms, also substituted by substituents inert under the reaction conditions, and X is either chlorine or bromine, is made to react with a salt of 3-butenoic acid of formula:

$$CH_2=CH-CH_2-COOM \quad (II)$$

wherein M represents a metal chosen from amongst Na, K, ½ Ca, ½ Mg or represents the group $NR'_4$ wherein ($R'_4$) represents alkyl groups having from 1 to 12 carbon atoms, in an organic medium and under an inert atmosphere, in the presence of a catalyst chosen from amongst phosphinic complexes of rhodium and nickel, at a temperature greater than about 50° C.

The reaction may for instance be represented by the following equation for 3,5-hexadienoic acid:

$$CH_2=CHX + CH_2=CH-CH_2-COOM \xrightarrow{cat.}$$
$$CH_2=CH-CH=CH-CH_2-COOH + MK.$$

In the above equation, the symbols have the same meanings as in formulas (I) and (II).

The same reaction develops analogously also for the other possible dienoic acids.

The reaction is conducted in an organic solvent capable of dissolving at least partially, either alone or in admixture with minor quantities of water, the salts of 3-butenoic acid.

Solvents suitable for the purpose include the hydrocarbons, the ethers, the esters, nitriles, amides, alcohols, ketones.

Just for illustrative purposes and for ease of separation of the reaction products, it is convenient to operate with solvents having a boiling point below about 150° C.

Thus, among the ethers may be chosen: butyl ether, and anisol; among the esters: ethyl acetate; among the nitriles: acetonitrile; among the amides: dimethylformamide; among the alcohols, ethyl alcohol; among the ketones: acetone and methylethylketone; among the hydrocarbons: toluene.

The reaction temperature is comprised between 50° C. and about 100° C. when complexed phosphinic catalysts of rhodium are used, and between 70° C. and about 120° C. when complexed phosphinic catalysts of nickel are used.

The catalyst is chosen between:

(A) a monovalent rhodium complex with hydrocarbylic phosphines having the formula:

$$RhCl(PR''_3)_x.(ol)_y$$

wherein R'' represents a hydrocarbylic group having from 1 to 8 carbon atoms; "ol" represents a simple olefin having from 2 to 8 carbon atoms or a chelating olefin having from 6 to 8 carbon atoms; x is an integer comprised between 1 and 3, while y is an integer chosen from between 0 and 2 in such a way that x+y=3; and (B) a zerovalent nickel complex with the same phosphines and having the formula:

$$Ni(PR''_3)_z$$

wherein R'' has the meaning already stated, and z is an integer which is 3 or 4.

Said Rh— and Ni— complexes are known and available on the market, or they may be obtained according to conventional methods, for instance by reduction of nickel or rhodium salts in the presence of the binder (phosphine), etc.

More particularly, effective results have been achieved by the use of complexes in which R'' is chosen from among: butyl, phenyl, anisyl; the olefin is chosen between ethylene and cyclooctene and the chelating olefin is 1,5-hexadiene or 1,5-cyclooctadiene.

As to the starting products, 3-butenoic acid is a compound industrially known as an intermediate, while the vinyl halides, likewise known, may be prepared according to known or conventional techniques.

The vinyl halides that are most interesting for the purposes of the reaction are those of the trans-type, especially when using the rhodium catalysts for which they are particularly effective.

Effective vinyl halides proved to be: vinyl bromide, styryl bromide and styryl bromides substituted in the aromatic nucleus, etc.

Among the catalysts, $RhCl(PPh_3)_3$ and $Ni(PPh_3)_3$ also proved to be effective.

The reactants are used in substantially stoichiometric molar ratios, while their concentration in the solvent is not critical for the purposes of the reaction. It is also possible to operate with an excess of the salt of 3-butenoic acid.

As already stated hereinabove, the reaction is a catalytic one. Catalyst quantities of the order of at least 0.1 millimols per liter of the reaction mixture are sufficient. The quantity of catalyst used may go up to about 100 millimols per liter.

As stated above, in the vinyl halide of formula (I) R—CH=CHX, R represents a hydrogen atom or a hydrocarbyl group having up to 20 carbon atoms. Said hydrocarbyl group may also in its turn be substituted with groups or atoms that are inert under the foreseen reaction conditions without interfering with them. Compatible substituents are, for instance, CN, $OCH_3$, $OCOCH_3$, etc.

The desired product is separated according to conventional techniques by acidification ($H_2SO_4$) after distillation of the solvent, extraction, etc.

According to one effective embodiment, the process of this invention is conducted in the following way:

Into a closed reactor and under a nitrogen atmosphere, at atmospheric pressure, there are introduced: the catalytic complex, the salt of 3-butenoic acid and the vinyl halide, and finally the chosen solvent. The solution thus obtained is maintained at the pre-established temperature for the required time. The mixture is then treated with a diluted inorganic acid, and the organic layer is separated by extraction with a solvent (ethyl ether).

By treatment of the organic extract with aqueous $Na_2CO_3$ and by a successive new acidification and extraction of the new aqueous phase, there are separated the acid part from which the acids are in their turn separated by distillation, etc.

The process, thanks to the mild operating conditions, is particularly convenient.

Other advantages consist in the availability of the starting compounds and in the selectivity of the reaction.

The invention will now be described in more detail by the following examples which are, however, given for merely illustrative purposes.

EXAMPLE 1

(This example includes also the preparation of sorbic acid from 3,5-hexadienoic acid. Ph stands for phenyl.)

Into a 250 cc flask were introduced under a nitrogen atmosphere 9 g of potassium 3-butenoate (7.2 $10^{-2}$ mols), 7.8 g of vinyl bromide (7.2 $10^{-2}$ mols) 0.3 g of $RhCl(PPh_3)_3$ (3.3 $10^{-4}$ mols) and lastly 90 cc of ethyl alcohol.

The mixture was heated to a temperature of 85° C. for about 48 hours.

The raw product was thereupon decomposed with diluted sulphuric acid and then extracted with ether. By a conventional treatment of the reaction mixture with a soda solution and by subsequent acidification, there were obtained 2.5 g of 3,5-hexadienoic acid.

By further treatment of the 3,5-hexadienoic acid with hot caustic soda at about 100° C., according to conventional methods, by isomerization there was obtained the formation of the sodium salt of sorbic acid, that is of 2,4-hexadienoic acid.

EXAMPLE 2

Following the same procedure as described in Example 1, into a 100 cc flask there were placed 4.1 g of potassium 3-butenoate (3.3 $10^{-2}$ mols), 6 g of styryl trans-bromide (I) (3.3 $10^{-2}$ mols), 0.1 g of $RhCl(PPh_3)_3$ (1.1 $10^{-4}$ mols) and 30 cc of ethyl alcohol. This mixture was heated up to 85° C. under nitrogen atmosphere for about 48 hours.

After decomposition with diluted sulphuric acid and after extraction with ether, there were obtained, by the given methods, about 4 g of 6-phenyl-3,5-hexadienoic acid, as a mixture of 3-cis-5-trans and 3-trans-5-trans isomers.

EXAMPLE 3

Proceeding as in Example 1, into a 100 cc flask were placed to react: 4.1 g of potassium 3-butenoate (3.3 $10^{-2}$ mols), 6 g of styryl bromide, a cis-trans mixture, (3.3 $10^{-2}$ mols), 2.9 g of $Ni(PPh_3)_3$ (3.3 $10^{-2}$ mols) and 40 cc of ethyl alcohol. The mass was heated up to 105° C. under nitrogen atmosphere, for about 2 hours. Operating as in Example 1, there were obtained 2.2 g of 6-phenyl-3,5-hexadienoic acid, a mixture of isomers containing double cis and trans bonds.

EXAMPLE 4

Example 2 was repeated but using styryl chloride (I) trans instead of styryl bromide. Thereby was obtained a mixture of 6-phenyl-3,5-hexadienoic acids.

EXAMPLE 5

Example 1 was repeated, but using 1-bromo-1-octene instead of vinyl bromide. Thereby was obtained a mixture of stereoisomers of 3,5-dodecadienoic acid.

What is claimed is:

1. A process for the preparation of dienoic acids having double bonds in a conjugated position, which process comprising reacting a vinyl halide of the formula: R—CH=CHX, wherein R is selected from the group consisting of hydrogen, hydrocarbylic groups having from 1 to 20 carbon atoms, and said hydrocarbylic groups substituted by substituents inert under the reaction conditions, and X is chlorine or bromine, with a salt of 3-butenoic acid of the formula: $CH_2$=CH—$CH_2$=COOM, wherein M is a metal selected from the group consisting of Na, K, ½ Ca, ½ Mg or the group $NR'_4$ wherein $(R')_4$ are alkyl groups having from 1 to 12 carbon atoms, in an organic medium and under an inert atmosphere, at a temperature above 50° C. and at atmospheric pressure, in the presence of a catalyst selected from the group consisting of phosphinic complexes of rhodium and nickel having the formulae:

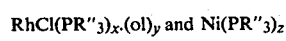

$RhCl(PR''_3)_x.(ol)_y$ and $Ni(PR''_3)_z$ wherein R" is a hydrocarbylic group having from 1 to 8 carbon atoms; "ol" is an olefin selected from the group consisting of olefins having a number of carbon atoms comprised between 2 and 8 and chelating olefins having 6 to 8 carbon atoms, and where x is an integer comprised between 1 and 3, y is an integer comprised between 0 and 2 and such that $x+y=3$, and z is a number comprised between 3 and 4.

2. The process of claim 1, in which the organic medium is selected from the group consisting of hydrocarbons, ethers, esters, nitriles, amides, alcohols and ketones.

3. The process of claim 2 in which the organic medium has a boiling point below about 150° C.

4. The process of claim 2, in which the organic medium is selected from the group consisting of ethyl alcohol, butyl ether, anisol, ethyl acetate, acetonitrile, dimethylformamide, acetone, methylethylketone and toluene.

5. The process of claim 1, in which the organic medium is used in admixture with minor quantities of water.

6. The process of claim 1, in which the catalyst is a phosphinic complex of rhodium and the reaction is carried out at a temperature comprised between 50° and about 100° C.

7. The process of claim 1, in which the catalyst is a phosphinic complex of nickel, and the reaction is carried out at temperatures comprised between 70° C. and about 100° C.

8. The process of claim 1, in which the catalyst is a complex of rhodium or nickel with a $(PR'')_3$ phosphine wherein R'' is selected from the group consisting of butyl, phenyl, anisyl, groups and the olefin is selected from the group consisting of ethylene, cyclooctene, 1,5-hexadiene and 1,5-cyclooctadiene.

9. The process of claim 1, in which the vinyl halide is selected from the group consisting of vinyl bromide and styryl bromide.

10. The process of claim 1, in which the catalyst is selected from the group consisting of $RhCl(PPh_3)_3$ and $Ni(PPh_3)_3$.

11. The process of claim 1, in which the vinyl halide and the salt of the 3-butenoic acid are made to react in substantially equimolar ratios.

12. The process of claim 1, in which the complexed rhodium or nickel catalyst is used in quantities at least equal to 0.1 millimols per liter of reacting mass and up to about 100 millimols per liter.

* * * * *